(12) United States Patent
Tetzlaff et al.

(10) Patent No.: US 6,277,117 B1
(45) Date of Patent: Aug. 21, 2001

(54) OPEN VESSEL SEALING FORCEPS WITH DISPOSABLE ELECTRODES

(75) Inventors: Philip Mark Tetzlaff, Golden; Steven Paul Buysse, Longmont; Kate Ryland Lawes, Superior; Dale Francis Schmaltz, Fort Collins, all of CO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/178,027

(22) Filed: Oct. 23, 1998

(51) Int. Cl.[7] .................................................. A61B 18/18
(52) U.S. Cl. ................................. 606/48; 606/51; 606/52
(58) Field of Search ................................. 606/41, 45, 48, 606/49–52, 174, 205, 206, 207

(56) References Cited

U.S. PATENT DOCUMENTS

| | | |
|---|---|---|
| 371,664 | 10/1887 | Brannan et al. . |
| 702,472 | 6/1902 | Pignolet . |
| 728,883 | 5/1903 | Downes . |
| 1,586,645 | 6/1926 | Bierman . |
| 2,002,594 | 5/1935 | Wappler et al. . |
| 2,176,479 | 10/1939 | Willis . |
| 3,643,663 | 2/1972 | Sutter . |
| 3,651,811 | 3/1972 | Hildebrandt et al. . |
| 3,920,021 | 11/1975 | Hiltebrandt . |
| 3,938,527 | 2/1976 | Rioux et al. . |
| 3,952,749 | 4/1976 | Fridolph et al. . |
| 4,005,714 | 2/1977 | Hiltebrandt . |
| 4,370,980 | 2/1983 | Lottick . |
| 4,552,143 | 11/1985 | Lottick . |
| 4,597,379 | 7/1986 | Kihn et al. . |
| 4,657,016 * | 4/1987 | Garito et al. ............................ 606/45 |
| 4,671,274 | 6/1987 | Sorochenko . |
| 4,685,459 | 8/1987 | Koch et al. . |
| 4,887,612 | 12/1989 | Esser et al. . |
| 4,938,761 | 7/1990 | Ensslin . |
| 5,026,370 | 6/1991 | Lottick . |
| 5,116,332 | 5/1992 | Lottick . |
| 5,151,102 | 9/1992 | Kamiyama et al. . |
| 5,217,458 | 6/1993 | Parins . |

(List continued on next page.)

FOREIGN PATENT DOCUMENTS

| | | |
|---|---|---|
| 0 584 787 A1 | 3/1994 | (EP) . |
| 0 853 922 A1 | 7/1998 | (EP) . |
| 401367 | 10/1973 | (SU) . |

OTHER PUBLICATIONS

Sigel et al., "The Mechanism of Blood Vessel Closure by High Frequency Electocoagulation", Surgery Gynecology & Obstetrics, Oct. 1965, pp. 823–831.
Bergdahl et al. "Studies on Coagulation and the Development of an Automation Computerized Bipolar Coagulator", *J. Neurosurg*, vol. 75, Jul. 1991, pp. 148–151.
International Search Report –PCT/US98/18640.
International Search Report –PCT/US98/23950.

*Primary Examiner*—Linda C. M. Dvorak
*Assistant Examiner*—R. Kearney

(57) ABSTRACT

A removable electrode assembly for use in combination with a forceps having opposing end effectors and a handle for effecting movement of the end effectors relative to one another. The electrode assembly includes a housing which is removably engageable with the forceps and a pair of electrodes which are attachable to a distal end of the housing. The electrodes are removably engageable with the end effectors of the forceps such that the electrodes reside in opposing relation relative to one another. The electrode assembly also includes a cover plate which is removably attachable to the housing and at least one stop member for controlling the distance the electrodes move relative to one another.

2 Claims, 7 Drawing Sheets

U.S. PATENT DOCUMENTS

| | | |
|---|---|---|
| 5,250,047 | 10/1993 | Rydell . |
| 5,258,006 | 11/1993 | Rydell et al. . |
| 5,261,918 * | 11/1993 | Philips et al. .................. 606/140 |
| 5,277,201 | 1/1994 | Stern . |
| 5,324,289 | 6/1994 | Eggers . |
| 5,330,471 | 7/1994 | Eggers . |
| 5,342,359 | 8/1994 | Rydell . |
| 5,352,222 | 10/1994 | Rydell . |
| 5,356,408 | 10/1994 | Rydell . |
| 5,389,104 | 2/1995 | Hahnen et al. . |
| 5,391,166 | 2/1995 | Eggers . |
| 5,403,312 | 4/1995 | Yates et al. . |
| 5,431,674 | 7/1995 | Basile et al. . |
| 5,443,463 | 8/1995 | Stern et al. . |
| 5,443,464 | 8/1995 | Russell et al. . |
| 5,445,658 | 8/1995 | Durrfeld et al. . |
| 5,456,684 | 10/1995 | Schmidt et al. . |
| 5,462,546 | 10/1995 | Rydell . |
| 5,472,443 | 12/1995 | Cordis et al. . |
| 5,478,351 | 12/1995 | Meade et al. . |
| 5,484,436 | 1/1996 | Eggers et al. . |
| 5,509,922 | 4/1996 | Aranyi et al. . |
| 5,527,313 | 6/1996 | Scott et al. . |
| 5,531,744 | 7/1996 | Nardella et al. . |
| 5,540,684 | 7/1996 | Hassler, Jr. . |
| 5,558,672 | 9/1996 | Edwards et al. . |
| 5,569,241 | 10/1996 | Edwards . |
| 5,573,535 | 11/1996 | Viklund . |
| 5,626,578 | 5/1997 | Tihon . |
| 5,637,110 | 6/1997 | Pennybacker et al. . |
| 5,658,281 | 8/1997 | Heard . |
| 5,667,526 | 9/1997 | Levin . |
| 5,674,220 | 10/1997 | Fox et al. . |
| 5,693,051 | 12/1997 | Schulze et al. . |
| 5,700,261 | 12/1997 | Brinkerhoff . |
| 5,702,390 | 12/1997 | Austin et al. . |
| 5,766,166 | 6/1998 | Hooven . |
| 5,769,849 | 6/1998 | Eggers . |
| 5,776,128 | 7/1998 | Eggers . |
| 5,776,130 | 7/1998 | Buysse et al. . |
| 5,827,281 | 10/1998 | Levin . |
| 5,951,549 * | 9/1999 | Richardson et al. .................. 606/45 |

* cited by examiner

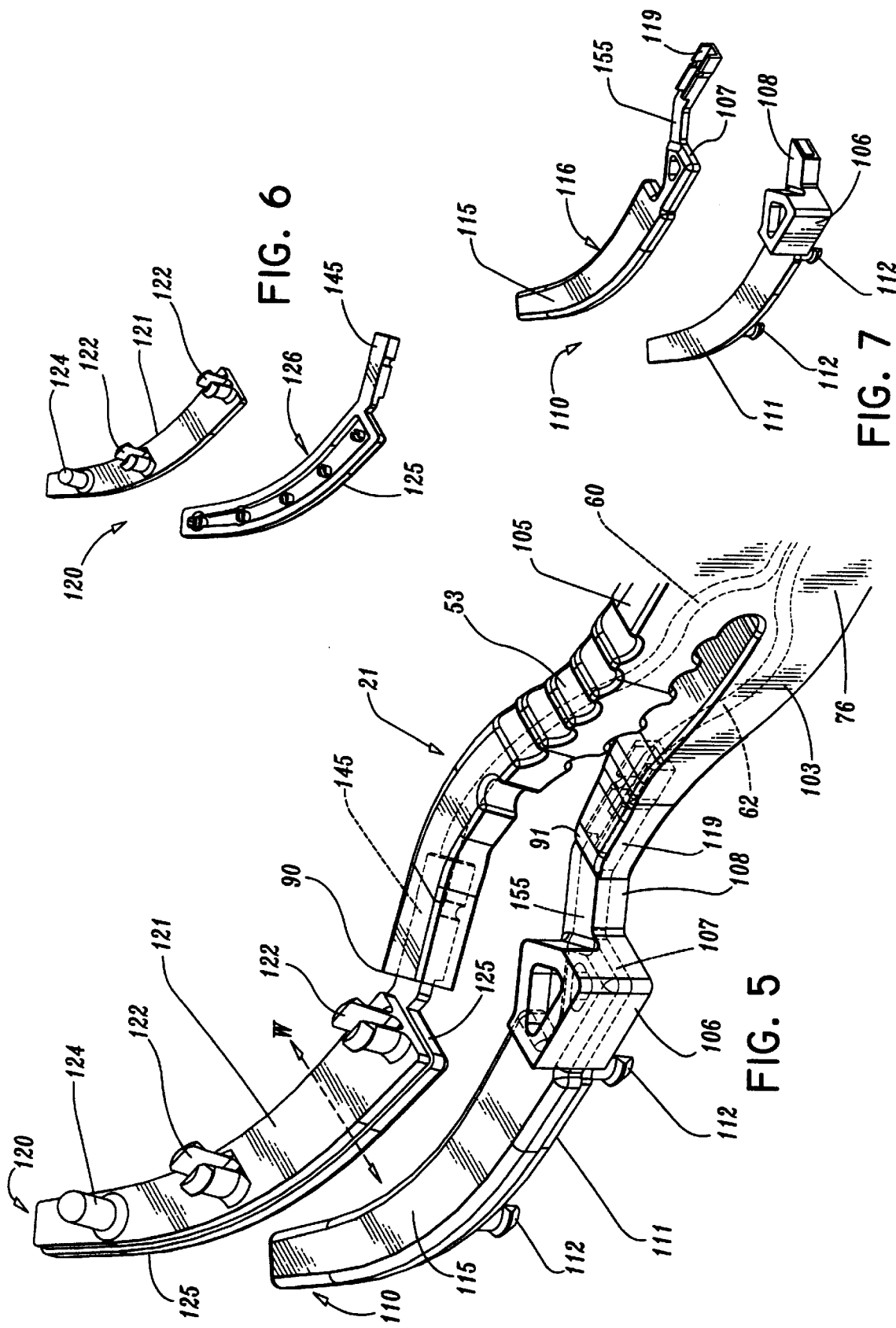

OPEN VESSEL SEALING FORCEPS WITH DISPOSABLE ELECTRODES

BACKGROUND

The present disclosure relates to electrosurgical forceps used for open surgical procedures. More particularly, the present disclosure relates to a bipolar forceps having a disposable electrode assembly for sealing, cauterizing, coagulating/desiccating and/or cutting vessels and vascular tissue.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize, cut and/or seal tissue.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of end effectors and which are both electrically coupled to an electrosurgical generator. Each electrode is charged to a different electric potential. Since tissue is a conductor of electrical energy, when the effectors are utilized to clamp or grasp tissue therebetween, the electrical energy can be selectively transferred through the tissue.

The process of coagulating small vessels is fundamentally different than vessel sealing. For the purposes herein the term coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to close them, however, larger vessels need to be sealed to assure permanent closure.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. No. 4,005,714 to Hiltebrandt, U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al., all relate to electrosurgical instruments for coagulating, cutting and/or sealing vessels or tissue.

These instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles.

Thus, a need exists to develop a bipolar forceps which can seal vessels and tissue consistently and effectively and which will not be damaged by continued use and cleaning.

SUMMARY

The present disclosure relates to a removable electrode assembly for use in combination with a mechanical forceps having opposed end effectors and a handle for controlling movement of the end effectors relative to one another. The electrode assembly includes a housing which is removably engageable with the mechanical forceps and a pair of electrodes which are attachable to a distal end of the housing. The electrodes are removably engageable with the end effectors of the mechanical forceps such that the electrodes reside in opposing relation relative to one another.

Preferably, the distal end of the housing is bifurcated forming two prongs and each of the electrodes is attached to each of the prongs. In one embodiment, the prongs are movable relative to one another to facilitate engagement of the electrodes with the end effectors of the mechanical forceps.

Each electrode preferably includes an electrically conductive sealing surface and an insulating substrate. The substrate includes at least one mechanical interface for engaging a complimentary mechanical interface disposed on the corresponding end effector of the mechanical forceps. In one embodiment the electrodes include at least one guide pin and the corresponding end effector includes a complimentary aperture for receiving the guide pin.

Preferably, the electrode assembly includes at least one stop member for controlling the distance between the opposing electrodes. In another embodiment of the present disclosure, the mechanical forceps includes at least one stop member for controlling the distance between the end effectors which, in turn, control the distance between the attached opposing electrodes.

Another embodiment of the present disclosure includes a cover plate which is removably engageable with the housing member and the mechanical forceps are disposed between the housing and the cover plate when the bipolar forceps is assembled.

BRIEF DESCRIPTION OF THE DRAWINGS

FIG. 5 is an enlarged, perspective view of a distal end of the disposable electrode assembly of FIG. 4;

FIG. 6 is a perspective view with parts separated of an upper electrode of the disposable electrode assembly of FIG. 5;

FIG. 7 is a perspective view with parts separated of a lower electrode of the disposable electrode assembly of FIG. 5;

DETAILED DESCRIPTION OF THE PREFERRED EMBODIMENTS

Figure 1:
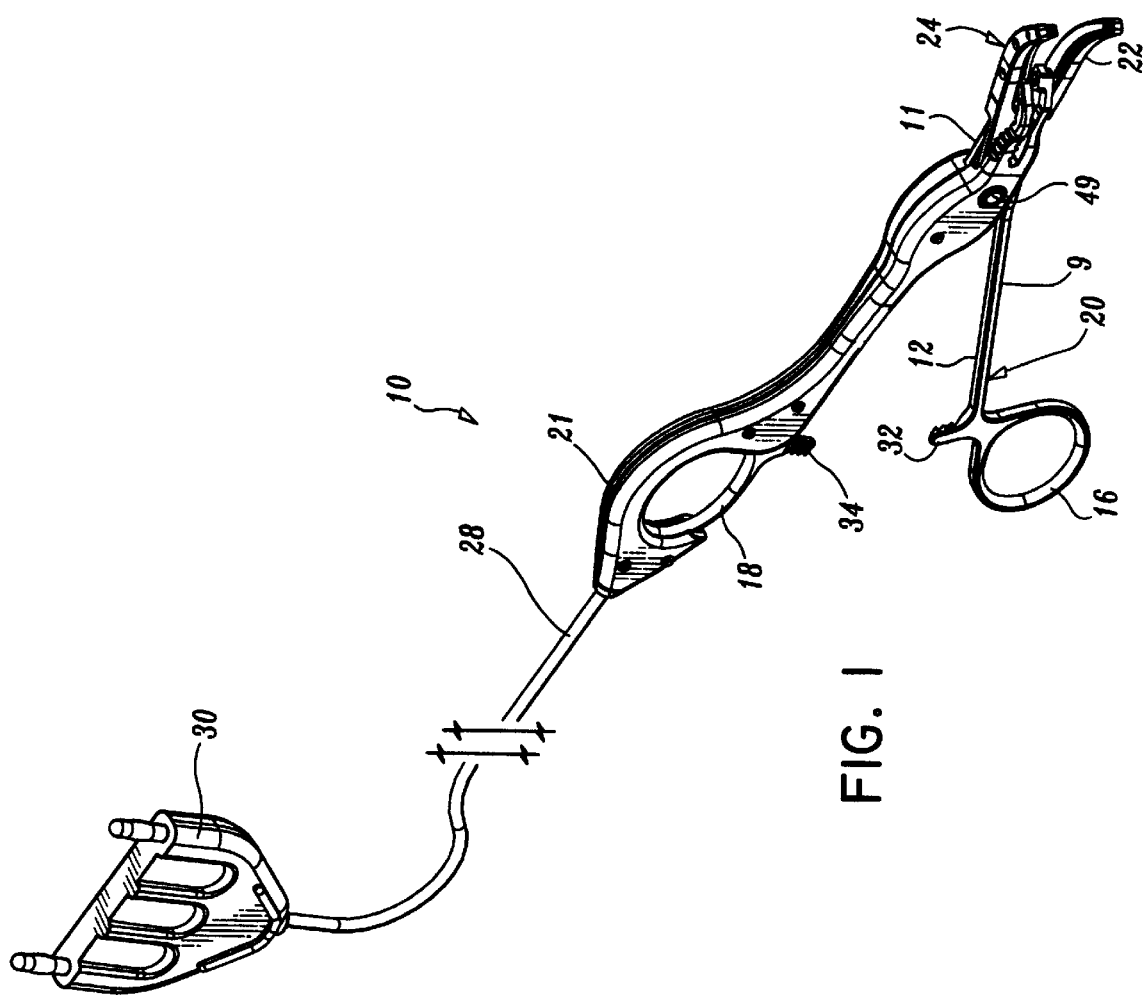
FIG. 1 is a perspective view of a bipolar forceps according to the present disclosure.
Figure 2:
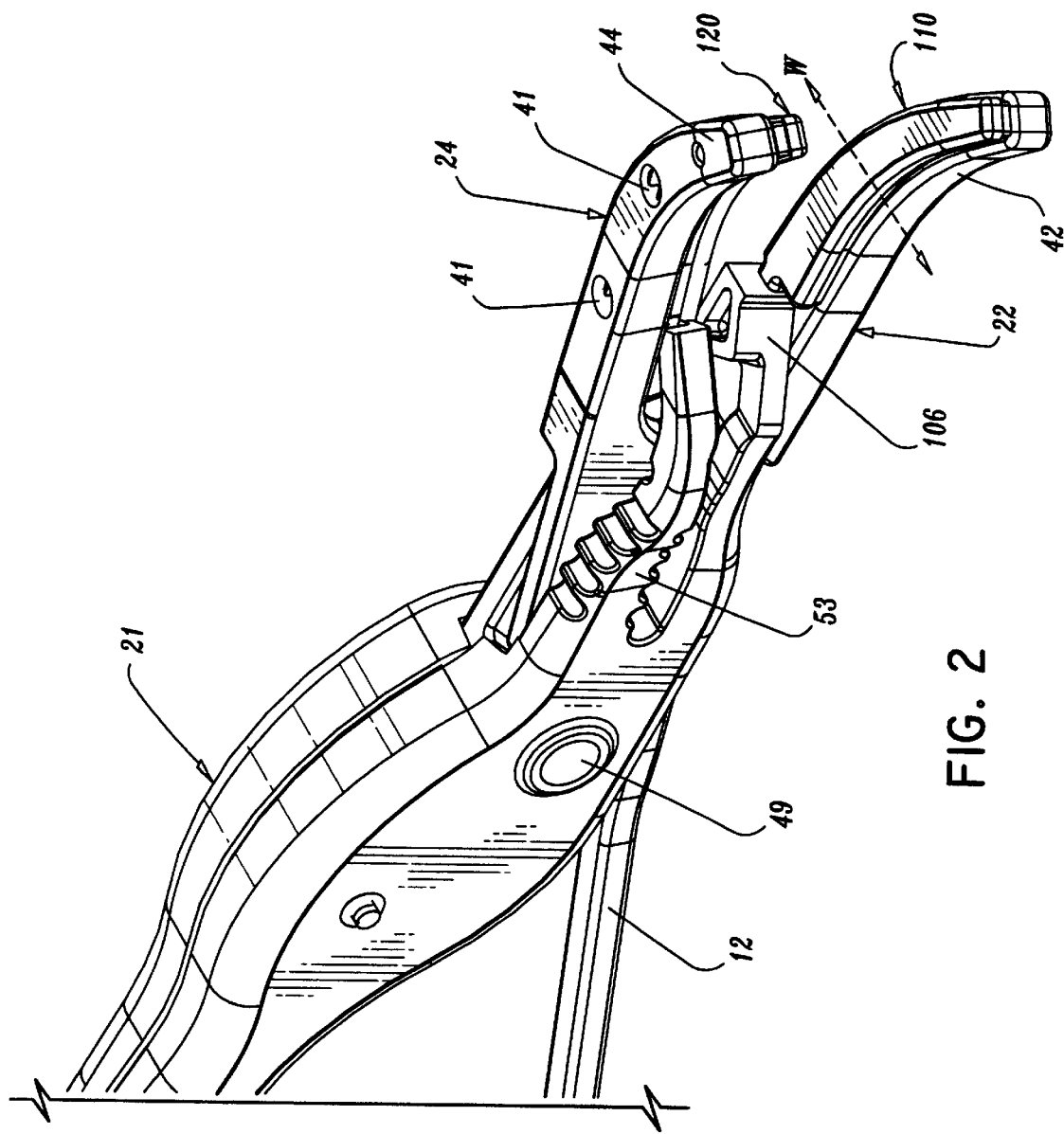
FIG. 2 is an enlarged, perspective view of a distal end of the bipolar forceps shown in FIG. 1.
Figure 3:
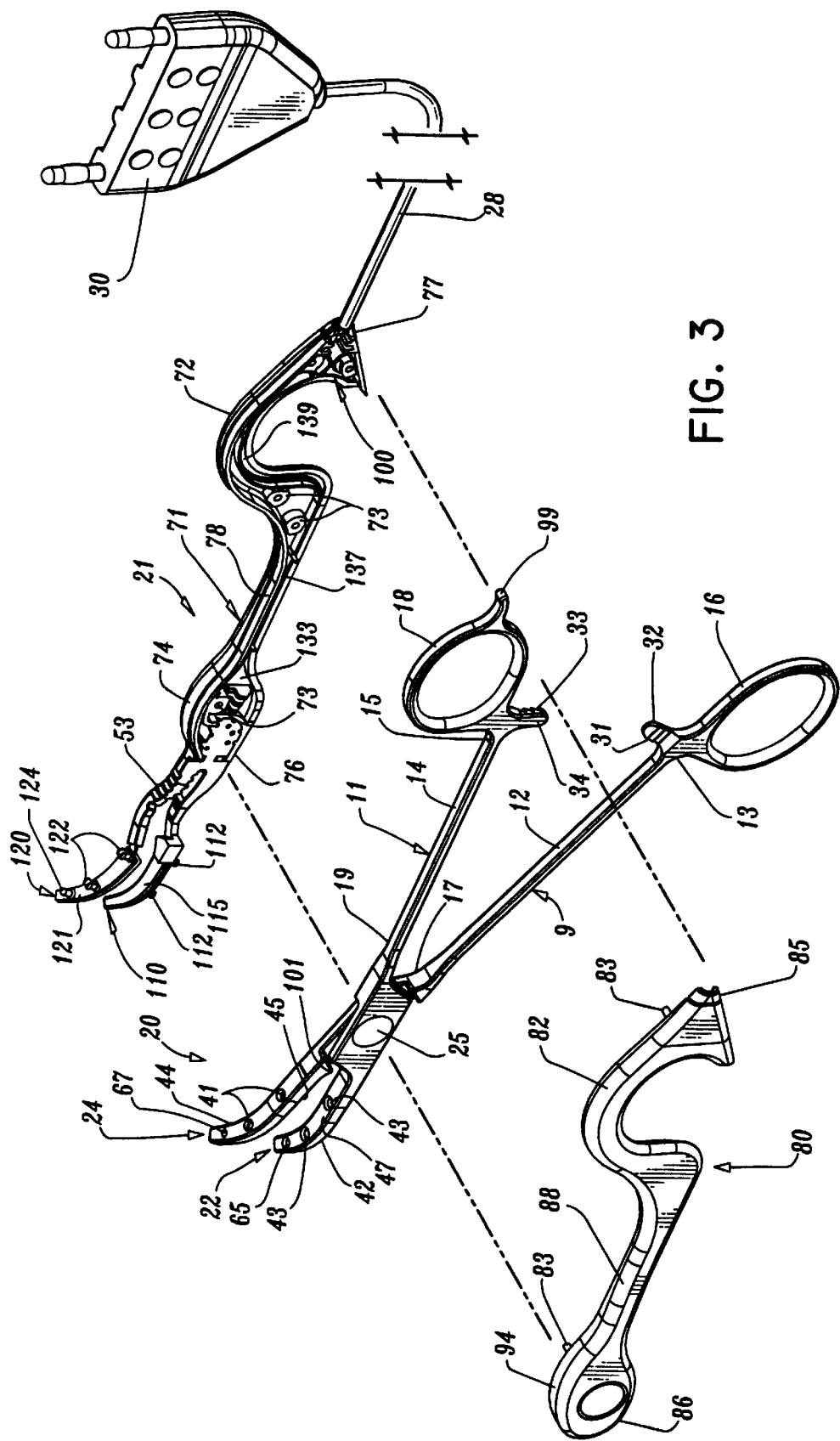
FIG. 3 is a perspective view with parts separated of the forceps shown in FIG. 1.

Referring now to FIGS. 1–3, a bipolar forceps 10 for use with open surgical procedures includes a mechanical forceps 20 and an electrode assembly 21. In the drawings and in the description which follows, the term "proximal", as is traditional, will refer to the end of the forceps 10 which is closer to the user, while the term "distal" will refer to the end which is further from the user.

Mechanical forceps 20 includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto to allow a user to effect movement of the two shaft portions 12 and 14 relative to one another. Extending from the distal end 17 and 19 of each shaft portion 12 and 14 are end effectors 22 and 24, respectively. The end effectors 22 and 24 are movable relative to one another in response to movement of handle members 16 and 18.

Figure 8:
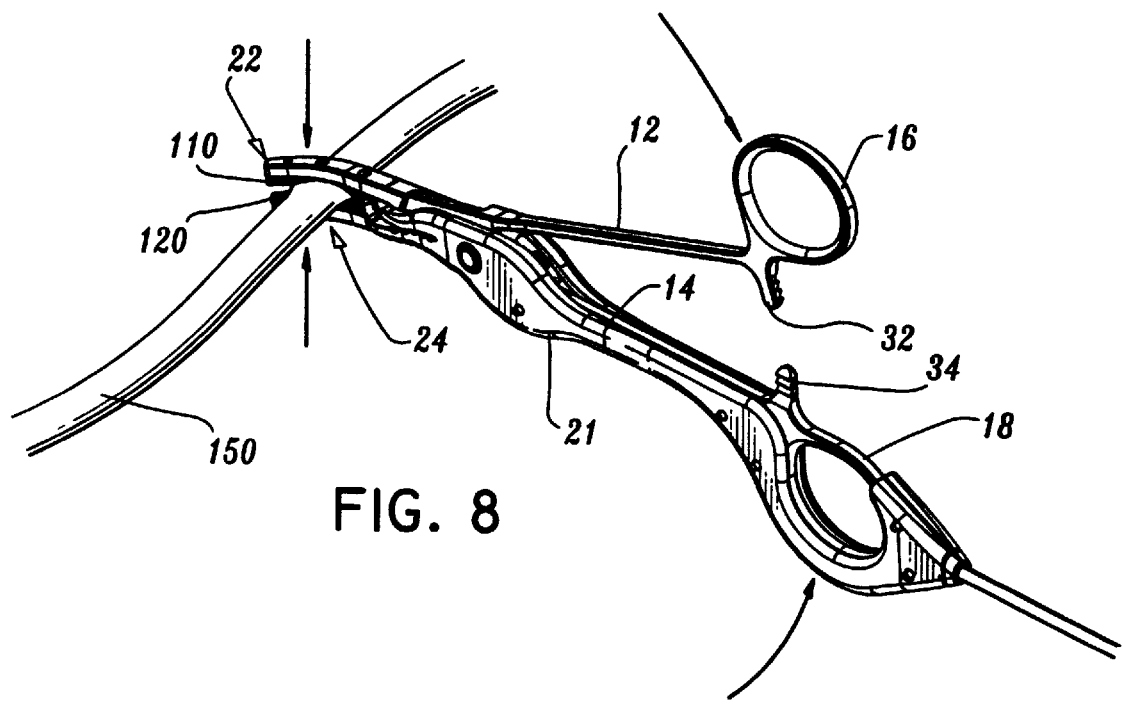
FIG. 8 is a perspective view of the forceps of the present disclosure showing the operative motion of the forceps to effect sealing of a tubular vessel.

Preferably, shaft portions 12 and 14 are affixed to one another at a point proximate the end effectors 22 and 24 about a pivot 25 such that movement of the handles 16 and 18 impart movement of the end effectors 22 and 24 from an open position wherein the end effectors 22 and 24 are disposed in spaced relation relative to one another to a clamping or closed position wherein the end effectors 22 and 24 cooperate to grasp a tubular vessel 150 therebetween (see FIG. 8). It is envisioned that pivot 25 has a large surface area to resist twisting and movement of forceps 10 during operation.

As best seen in FIG. 3, end effector 24 includes an upper or first jaw member 44 which has an inner facing surface 45 and a plurality of mechanical interfaces disposed thereon which are dimensioned to releasable engage a portion of a disposable electrode assembly 21 which will be described in greater detail below. Preferably, the mechanical interfaces include sockets 41 which are disposed at least partially through inner facing surface 45 of jaw member 44 and which are dimensioned to receive a complimentary detent attached to upper electrode 120 of the disposable electrode assembly 21. While the term socket is used herein, it is contemplated that either a male or female mechanical interface may be used on jaw member 44 with a mating mechanical interface disposed on the disposable electrode assembly 21.

In some cases, it may be preferable to manufacture mechanical interfaces 41 along another side of jaw member 44 to engage a complimentary mechanical interface of the disposable electrode assembly 21 in a different manner, e.g., from the side. Jaw member 44 also includes an aperture 67 disposed at least partially through inner face 45 of end effector 24 which is dimensioned to receive a complimentary guide pin 124 disposed on electrode 120 of the disposable electrode assembly 21.

End effector 22 includes a second or lower jaw member 42 which has an inner facing surface 47 which opposes inner facing surface 45. Preferably, jaw members 45 and 47 are dimensioned generally symmetrically, however, in some cases it may be preferable to manufacture the two jaw members 42 and 44 asymmetrically depending upon a particular purpose. In much the same fashion as described above with respect to jaw member 44, jaw member 42 also includes a plurality of mechanical interfaces or sockets 43 disposed thereon which are dimensioned to releasable engage a complimentary portion disposed on an electrode 110 of the disposable electrode assembly 21 as described below. Likewise, jaw member 42 also includes an aperture 65 disposed at least partially through inner face 47 which is dimensioned to receive a complimentary guide pin 126 (see FIG. 4) disposed on electrode 110 of the disposable electrode assembly 21.

Preferably, shaft members 12 and 14 of the mechanical forceps 20 are designed to transmit a particular desired force to the opposing inner facing surfaces 47 and 45 of the of the jaw members 22 and 24, respectively, when clamped. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34. Preferably, each ratchet, e.g., 32, extends from the proximal end 13 of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. Preferably, each ratchet position holds a specific, i.e., constant, strain energy in the shaft members 12 and 14 which, in turn, transmit a specific force to the end effectors 22 and 24 and, thus, the electrode 120 and 110. A design without a ratchet system or similar system would require the user to hold the jaw members 42 and 44 together by applying constant force to the handles 16 and 18 which may yield inconsistent results.

In some cases it may be preferable to include other mechanisms to control and/or limit the movement of the jaw members 42 and 44 relative to one another. For example, a ratchet and pawl system could be utilized to segment the movement of the two handles into discrete units which will, in turn, impart discrete movement to the jaw members 42 and 44 relative to one another.

Preferably, at least one of the shaft members, e.g., 14, includes a tang 99 which facilitates manipulation of the forceps 20 during surgical conditions as well as facilitates attachment of electrode assembly 21 on mechanical forceps 20 as will be described in greater detail below.

As best seen in FIGS. 2, 3 and 5, disposable electrode assembly 21 is designed to work in combination with mechanical forceps 20. Preferably, electrode assembly 21 includes housing 71 which has a proximal end 77, a distal end 76 and an elongated shaft plate 78 disposed therebetween. A handle plate 72 is disposed near the proximal end 77 of housing 71 and is sufficiently dimensioned to releasably engage and/or encompass handle 18 of mechanical forceps 20. Likewise, shaft plate 78 is dimensioned to encompass and/or releasably engage shaft 14 and pivot plate 74 disposed near the distal end 76 of housing 71 is dimensioned to encompass pivot 25 and at least a portion of distal end 19 of mechanical forceps 20. It is contemplated that the electrode assembly 21 can be manufactured to engage either the first or second members 9 and 11 of the mechanical forceps 20 and their respective component parts 12, 16 or 14, 18, respectively.

In the embodiment shown in FIG. 2, handle 18, shaft 14, pivot 25 and a portion of distal end 19 are all dimensioned to fit into corresponding channels located in housing 71. For example, a channel 139 is dimensioned to receive handle 18, a channel 137 is dimensioned to receive shaft 14 and a channel 133 is dimensioned to receive pivot 25 and a portion of distal end 19.

Electrode assembly 21 also includes a cover plate 80 which is also designed to encompass and/or engage mechanical forceps 20 in a similar manner as described with respect to the housing 71. More particularly, cover plate 80 includes a proximal end 85, a distal end 86 and an elongated shaft plate 88 disposed therebetween. A handle plate 82 is disposed near the proximal end 85 and is preferably dimensioned to releasable engage and/or encompass handle 18 of mechanical forceps 20. Likewise, shaft plate 88 is dimensioned to encompass and/or releasable engage shaft 14 and a pivot plate 94 disposed near distal end 86 is designed to encompass pivot 25 and distal end 19 of mechanical forceps 20. Preferably, handle 18, shaft 14, pivot 25 and distal end 19 are all dimensioned to fit into corresponding channels (not shown) located in cover plate 80 in a similar manner as described above with respect to the housing 71.

Figure 4:
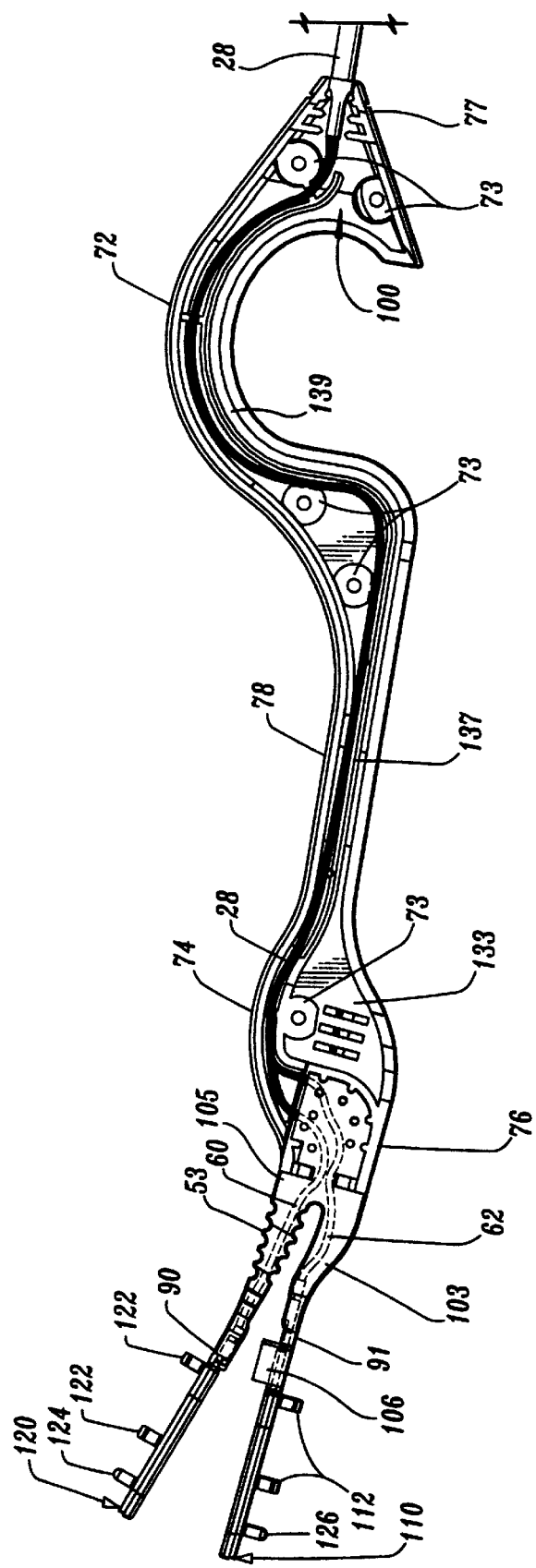
FIG. 4 is an enlarged, side view of a disposable electrode assembly of FIG. 1 shown without a cover plate.

As best seen with respect to FIGS. 3 and 4, housing 71 and cover plate 80 are designed to engage one another over first member 11 of mechanical forceps 20 such that first member 11 and its respective component parts, e.g., handle 18, shaft 14, distal end 19 and pivot 25, are disposed therebetween. Preferably, housing 71 and cover plate 80 include a plurality of mechanical interfaces disposed at various positions along the interior of housing 71 and cover plate 80 to effect mechanical engagement with one another. More particularly, a plurality of sockets 73 are disposed proximate handle plate 72, shaft plate 78 and pivot plate 74 of housing 71 and are dimensioned to releasably engage a corresponding plurality of detents 83 extending from cover plate 80. It is envisioned that either male or female mechanical interfaces or a combination of mechanical interfaces may be disposed within housing 71 with mating mechanical interfaces disposed on or within cover plate 80.

As best seen with respect to FIGS. 5–7, the distal end 76 of electrode assembly 21 is bifurcated such that two prong-like members 103 and 105 extend outwardly therefrom to support an electrode 110 and 120, respectively. More particularly, electrode 120 is affixed at an end 90 of prong 105 and electrode 110 is affixed at an end 91 of prong 103. It is envisioned that the electrodes 110 and 120 can be affixed to the ends 91 and 90 in any known manner such as, e.g., frictional or snap-fit engagement.

A pair of wires 60 and 62 are connected to the electrodes 120 and 110, respectively, as best seen in FIGS. 4 and 5. Preferably, wires 60 and 62 are bundled together and form a wire bundle 28 which runs from a terminal connector 30 (see FIG. 3), to the proximal end 77 of housing 71, along the interior of housing 71, to distal end 76. Wire bundle 28 is separated into wires 60 and 62 proximate distal end 76 and the wires 60 and 62 are connected to each electrode 120 and 110, respectively. In some cases it may be preferable to capture the wires 60 and 62 or the wire bundle 28 at various pinch points along the inner cavity of the electrode assembly 21 and enclosing the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases it may be preferable to extend wires 60 and 62 to an electrosurgical generator (not shown). Alternatively, wires 60 and 62 can remain separated and extend along the first and second members 9 and 11.

As best seen in FIG. 6, electrode 120 includes an electrically conductive seal surface 126 and an electrically insulative substrate 121 which are attached to one another by snap-fit engagement or some other method of assembly, e.g., substrate 121 is overmolded to capture the electrically conductive seal surface 126. Preferably, substrate 121 is made from an injection molded plastic material and is shaped to mechanically engage a corresponding socket 41 located in jaw member 44 of end effector 24. The substrate 121 not only insulates the electric current but it also aligns electrode 120 both of which contribute to the seal quality and consistency. For example, by overmolding the conductive surface 126 to the substrate 121, the alignment and thickness of the electrode 120 can be controlled.

Preferably, substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44.

Conductive seal surface 126 includes an wire crimp 145 designed to engage the distal end 90 of prong 105 of electrode assembly 21 and electrically engage a corresponding wire connector affixed to wire 60 located within electrode assembly. Seal surface 126 also includes an opposing face 125 which is designed to conduct an electrosurgical current to a tubular vessel or tissue 150 when it is held thereagainst.

Electrode 110 includes similar elements for insulating and conducting electrosurgical current to tissue 150. More particularly, electrode 110 includes an electrically conductive seal surface 116 and an electrically insulative substrate 111 which are attached to one another by snap-fit engagement or some other method of assembly. Substrate 111 includes a plurality of bifurcated detents 112 and an alignment pin 126 (see FIG. 4) which are dimensioned to engage a corresponding plurality of sockets 43 and aperture 65 located in jaw member 42. Conductive seal surface 116 includes an extension 155 having a wire crimp 119 which engages the distal end 91 of prong 103 and electrically engages a corresponding wire connector affixed to wire 62 located in housing 71. Seal surface 116 also includes an opposing face 115 which conducts an electrosurgical current to a tubular vessel or tissue 150 when it is held thereagainst. Alternatively, electrodes 110 and/or 120 can be formed as one piece and include similar components for insulating and conducting electrical energy.

As best seen in FIG. 7, substrate 111 also includes an extension 108 and a stop member 106 which is designed to engage corresponding extension 155 and an interface 107 located on conductive seal 116. To assemble electrode 110, stop member 106 and extension 108 are overmolded onto interface 107 and extension 155 of conductive seal 116. After assembly, wire crimp 119 is then inserted into end 91 of prong member 103 and connected to wire 62.

Two mechanical factors play an important role in determining seal thickness and effectiveness, i.e., the pressure applied between opposing faces 47 and 45 and the gap between the opposing electrodes 110 and 120 (see FIG. 5). Jaw members 42 and 44 are configured to provide for the opposing electrodes 110 and 120 to be in a desired gap range (e.g., 0.001 and 0.006 inches) at the end of the tissue sealing process. The material conditions and components relating to the assembly of the electrode assembly 21 and the mechanical forceps 20 are configured to fall within specific manufacturing tolerances to assure that the gap between electrodes will not vary outside the desired range.

It is known that tissue thickness is very difficult to control by force alone, i.e., too much force and the two poles would touch and the little energy would travel through the tissue resulting in a bad seal or too little force and the seal would be too thick. Applying the correct force is important for other reasons: to oppose the vessel lumens; reduce the tissue impedance to a low enough value that allows enough current through the tissue; and to overcome the forces of expansion during tissue heating in addition to contributing towards creating the required end tissue thickness which is an indication of a good seal.

In order to assure that the desired gap range is achieved after assembly and that the correct force is applied to seal the tissue, substrate 111 also includes at least one stop member, 106, which is designed to restrict and/or regulate movement of the two electrodes 110 and 120 relative to one another. Preferably, forceps 20 also includes at least one stop member, e.g., 101 (see FIG. 3), for restricting and/or regulating the distance between end effectors 22 and 24 and/or the closure force applied between opposing inner facing surfaces 47 and 45 of end effectors 22 and 24 which will, in turn, regulate the distance between electrodes 110 and 120. Since stop 106 is part of the disposable electrode assembly 21, this stop has the added benefit of being dependent on the material of the disposable electrode assembly 21. Preferably, a "step" stop is utilized due to its ease of manufacture and simplicity.

Preferably, the seal surfaces 115 and 125 are relatively flat to avoid current concentrations at sharp edges and to avoid arcing between high points. In addition and due to the reaction force of the tissue 150 when engaged, jaw members 42 and 44 are preferably manufactured to resist bending. For example and as best seen in FIG. 3, the jaw members 42 and 44 and the corresponding electrodes 110 and 120 are preferably tapered along width "W" which is advantageous for two reasons: 1) the taper will apply constant pressure for a constant tissue thickness at parallel; 2) the thicker proximal portion of the electrode, e.g., 110, will resist bending due to the reaction force of the tissue 150. The tapered shape of the electrode, e.g., 110, is determined by calculating the mechanical advantage variation from the distal to proximal end of the electrode 110 and adjusting the width of the electrode 110 accordingly.

Preferably, at least one of the prong members, e.g., 105, is resilient or includes a flex relief portion 53 which permits movement of the two prong members 105 and 103 and, thus, the two electrodes 120 and 110, relative to one another. As seen best in FIG. 3, the electrode assembly 21 is removably attached to the mechanical forceps 20 by initially moving prong 105 towards prong 103 by bending prong 105 at flex relief portion 53. The electrodes 110 and 120 are then slid between opposing jaw members 42 and 44 in their open position such that detents 112 and 122 and guide pins 126 and 124, respectively, are each disposed in alignment with each corresponding socket 43 and 41 or aperture 65 and 67, respectively. Housing 71 is also positioned accordingly such that shaft 14, handle 18 and pivot 25 are all positioned proximate their corresponding channels 137, 139 and 133 located within housing 71.

When flex relief portion 53 is released, each electrode 110 and 120 is engaged with jaw member 42 and 44, respectively, i.e., detents 112, 122 engage sockets 43, 41, and housing 71 is engaged with mechanical forceps 20. The cover plate 80 is then attached to housing 71 in the manner described above. The bipolar forceps 10 is now ready for operation.

In one embodiment, the electrode assembly 21 is attached to the mechanical forceps 20 in a different manner: For example and as best illustrated in FIG. 3, the electrode assembly 21 can be engaged with the mechanical forceps 20 in the following four-step manner: 1) electrode assembly 21 and cover plate 80 are pivoted backward such that tang 99 engages a slot 100 in electrode assembly 21; 2) electrode assembly 21 and cover plate 80 are then pivoted forward to engage shaft 14 of mechanical forceps 20 therebetween; 3) detents 112 of electrode 110 are then engaged with sockets 43 of jaw member 22; and 4) detents 122 of electrode 120 are engaged with sockets 41 of jaw member 24.

Figure 9:
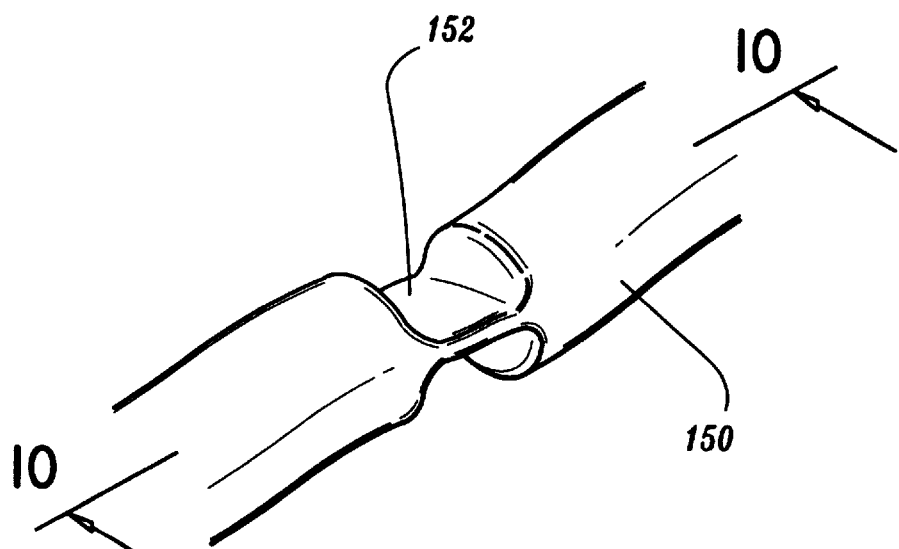
FIG. 9 is an enlarged, partial perspective view of a sealing site of a tubular vessel.
Figure 10:
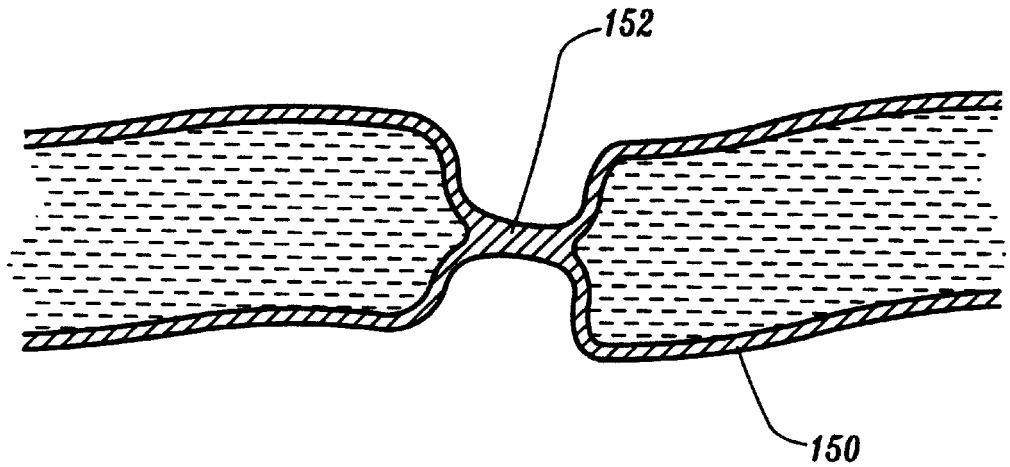
FIG. 10 is a longitudinal cross-section of the sealing site taken along line 10—10 of FIG. 9.
Figure 11:
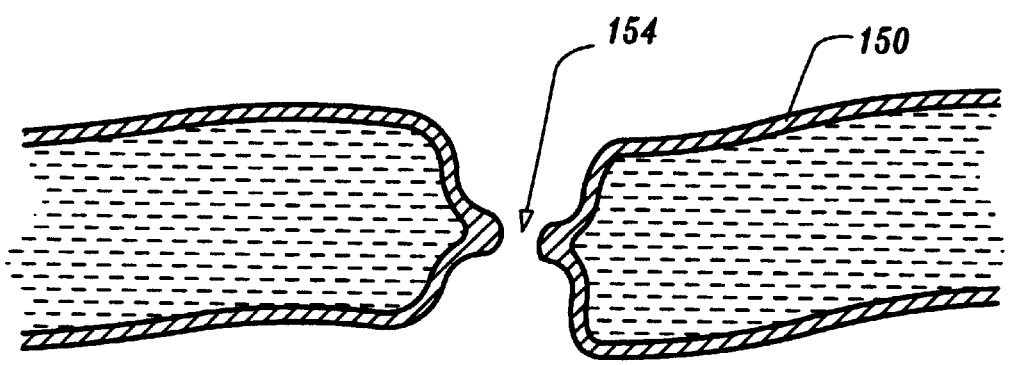
FIG. 11 is a longitudinal cross-section of the sealing site of FIG. 9 after separation of the tubular vessel.

FIG. 8 shows the bipolar forceps 10 during use wherein the handle members 16 and 18 are moved closer to one another to apply clamping force to the tubular tissue 150 to effect a seal 152 as shown in FIGS. 9 and 10. Once sealed, the tubular vessel 150 can be cut along seal 152 to separate the tissue 150 and form gap 154 therebetween as shown in FIG. 11.

After the bipolar forceps 10 is used or if the electrode assembly 21 is damaged, the electrode assembly 21 can be easily removed and/or replaced by reversing the above attachment procedure and a new electrode assembly 21 can be engaged with the mechanical forceps 20 in the same manner. For example, the electrode assembly 21 can be disengaged from the mechanical forceps 20 in the following four-step manner: 1) the detents 122 of electrode 120 are disengaged from the sockets 41 of jaw member 24; 2) the detents 112 of electrode 110 are disengaged from the sockets 43 of jaw member 22; 3) the electrode assembly 21 and cover plate 80 are disengaged from shaft 14 of mechanical forceps 20; and 4) the electrode assembly 21 and cover plate 80 are pivoted such that tang 99 disengages from slot 100 in electrode assembly 21.

It is envisioned that by making the electrode assembly 21 disposable, the electrode assembly 21 is less likely to become damaged since it is only intended for a single use and, therefore, does not require cleaning or sterilization. As a result, the functionality and consistency of the vital sealing components, e.g., the conductive surface 126, 116 and insulating surface 121, 111 will assure a uniform and quality seal.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16 and 18 is required to deflect the electrodes in the same plane.

Although it is preferable to vertically align electrodes 110 and 120, in some cases it may be preferable to offset the opposing electrodes 110 and 120 relative to one another either longitudinally or transversally to suit a particular purpose.

Although it is preferable that the electrode assembly 21 include housing 71 and cover plate 80 to engage mechanical forceps 20 therebetween, in some cases it may be preferable to manufacture the disposable electrode assembly 21 such that only one piece, e.g., housing 71 is required to engage mechanical forceps 20.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplications of a preferred embodiment. Those skilled in the art will envision other modifications within the scope and spirit of the claims appended hereto.

What is claimed is:

1. A removable electrode assembly for use with a forceps having opposing end effectors and a handle for effecting movement of the end effectors relative to one another, comprising:

a cover plate;

a housing having at least one portion which is removably engageable with at least one portion of the forceps;

a pair of electrodes attachable to a distal end of the housing, the electrodes being removably engageable with the end effectors of the forceps such that the electrodes reside in opposing relation relative to one another;

at least one stop member for controlling the distance between the opposing electrodes; and wherein both the cover plate and the housing are removably engageable with the forceps.

2. A removable electrode assembly according to claim 1 wherein the forceps are disposed between the housing and the cover plate.

* * * * *